United States Patent
Yamago et al.

(10) Patent No.: US 8,076,430 B2
(45) Date of Patent: Dec. 13, 2011

(54) LIVING RADICAL POLYMERIZATION PROMOTER

(75) Inventors: Shigeru Yamago, Osaka (JP); Kunihiko Sugoh, Tokushima (JP); Hikaru Umemoto, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 176 days.

(21) Appl. No.: 12/449,969

(22) PCT Filed: Mar. 6, 2008

(86) PCT No.: PCT/JP2008/054554
§ 371 (c)(1),
(2), (4) Date: Sep. 4, 2009

(87) PCT Pub. No.: WO2008/108500
PCT Pub. Date: Sep. 12, 2008

(65) Prior Publication Data
US 2010/0022728 A1    Jan. 28, 2010

(30) Foreign Application Priority Data
Mar. 7, 2007    (JP) ................................ 2007-057844

(51) Int. Cl.
C08F 4/20     (2006.01)
C07F 9/00     (2006.01)
C09K 3/00     (2006.01)

(52) U.S. Cl. ...... 526/190; 526/222; 556/70; 252/182.14

(58) Field of Classification Search .................. 526/190, 526/222; 556/70; 252/182.14
See application file for complete search history.

(56) References Cited

U.S. PATENT DOCUMENTS 7,847,043 B2 * 12/2010 Yamago et al. ............... 526/190
2007/0265404 A1 * 11/2007 Yamago et al. ............... 526/190

FOREIGN PATENT DOCUMENTS

| JP | 63-174926 | 7/1988 |
| JP | 2006-225524 | 8/2006 |
| WO | 2006-062255 | 6/2006 |
| WO | WO 2006062255 A1 * | 6/2006 |

OTHER PUBLICATIONS

D. Atwood et al., Synthesis and Structural Characterization of a Homoleptic Bismuth Arenethiolate, Inorg. Chem., 1993, vol. 32, p. 2972-297.*
W. Clegg et al, Neutral Thiolates of Antimony(III) and Bismuth(III), J. Chem. Soc. Dalton Trans., 1995, No. 13, pp. 2129-2135.*
D. Atwood et al., Synthesis and Structural Characterization of a Homoleptic Bismuth Arenethiolate, Inorg. Chem., 1993, vol. 32, pp. 2972-2974.*
International Search Report issued Apr. 15, 2008 in International (PCT) Application No. PCT/JP2008/054554, filed Mar. 6, 2008.
D. A. Atwood et al., "Synthesis and Structural Characterization of a Homoleptic Bismuth Arenethiolate", Inorg. Chem., vol. 32, pp. 2972-2974, 1993.
W. Clegg et al., "Neutral Thiolates of Antimony(III) and Bismuth(III)", J. Chem. Soc. Dalton Trans., Issue 1, No. 13, pp. 2129-2135, 1995.

* cited by examiner

*Primary Examiner* — Michael M Bernshteyn
(74) *Attorney, Agent, or Firm* — Wenderoth, Lind & Ponack, L.L.P.

(57) ABSTRACT

An organobismuth compound represented by the formula (1) and a method for preparing a living radical polymer using the organobismuth compound. In the formula (1), $R^1$ to $R^3$ each represent a C1-C8 alkyl group, an aryl group, a substituted aryl group, an aromatic heterocyclic group or a group represented by the formula (2) where at least one of $R^1$ to $R^3$ is a group represented by the formula (2), wherein $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

9 Claims, No Drawings

LIVING RADICAL POLYMERIZATION PROMOTER

This application is a U.S. national stage of International Application No. PCT/JP2008/054554 filed Mar. 6, 2008.

TECHNICAL FIELD

This invention relates to radical polymerization promoters and a method for preparing living radical polymers using the promoters.

BACKGROUND ART

Living radical polymerization is a polymerization technique that enables precise control of molecular structures while maintaining the convenience and versatility of radical polymerization, and makes a significant contribution to the syntheses of novel polymeric materials.

The inventors have reported, as an example of living radical polymerization, a living radical polymerization method using an organobismuth compound as an initiator (see for example Patent Document 1).

[Patent Document 1] WO 2006/62255

The method in Patent Document 1 makes it possible to control molecular weights and molecular weight distributions. However, in preparing high-molecular weight polymers having a number average molecular weight of 100000 or more, their molecular weight distributions may be wider than, but not more than 1.5, those of low-molecular weight polymers.

A purpose of the present invention is to provide a living radical polymerization promoter that enables precise control of the molecular weight and molecular weight distribution (PDI=Mw/Mn) of even a high-molecular weight polymer having a number average molecular weight of 100000 or more by polymerizing a vinyl monomer using an organobismuth compound represented by the formula (1) as the living radical polymerization promoter.

DISCLOSURE OF THE INVENTION

The present invention relates to the following aspects.
1. An organobismuth compound represented by the formula (1)

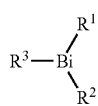
(1)

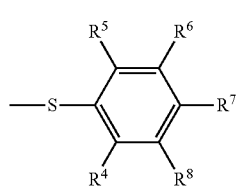
(2)

wherein $R^1$ to $R^3$ each represent a C1-C8 alkyl group, an aryl group, a substituted aryl group, an aromatic heterocyclic group or a group represented by the formula (2) where at least one of $R^1$ to $R^3$ is a group represented by the following formula (2)

wherein $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

2. A method for preparing an organobismuth compound, the method including reacting a compound represented by the formula (3) with a compound represented by the formula (4)

(3)

wherein X represents a halogen atom, a C1-C8 alkyl group, an aryl group, a substituted aryl group or an aromatic heterocyclic group where at least one of Xs is a halogen atom,

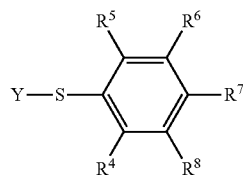
(4)

wherein Y represents a hydrogen atom or an alkali metal, $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

3. A radical polymerization promoter being a compound represented by the formula (1).

4. A method for preparing a living radical polymer, the method including polymerizing a vinyl monomer using a living radical polymerization initiator and a compound represented by the formula (1).

5. A living radical polymer obtained by polymerizing a vinyl monomer using a living radical polymerization initiator and a compound represented by the formula (1).

6. A mixture of a living radical polymerization initiator and a compound represented by the formula (1).

The organobismuth compound of the present invention is represented by the formula (1)

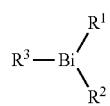
(1)

wherein $R^1$ to $R^3$ each represent a C1-C8 alkyl group, an aryl group, a substituted aryl group, an aromatic heterocyclic group or a group represented by the formula (2) where at least one of $R^1$ to $R^3$ is a group represented by the following formula (2)

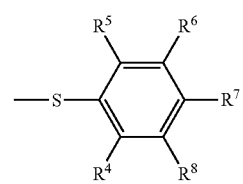
(2)

wherein $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

Specific examples of the groups represented by $R^1$ to $R^3$ are as follows.

Examples of the C1-C8 alkyl group include straight-chain, branched-chain and cyclic alkyl groups with 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl groups.

Preferable alkyl groups are straight- and branched-chain alkyl groups with 1 to 4 carbon atoms.

More preferable are methyl, ethyl and n-butyl groups.

Examples of the aryl group include phenyl and naphtyl groups.

A preferable aryl group is a phenyl group.

Examples of the substituted aryl group include substituent-containing phenyl and substituent-containing naphtyl groups.

Examples of the substituent in such a substituent-containing aryl group include a halogen atom, hydroxy, alkoxy, amino, nitro and cyano groups, a carbonyl-containing group represented by —COR$^a$ (R$^a$=a C1-C8 alkyl group, an aryl group, a C1-C8 alkoxy group or an aryloxy group), a sulfonyl group, and a trifluoromethyl group.

A preferable substituted aryl group is a trifluoromethyl-substituted phenyl group.

The number of substituents is preferably one or two, and the position of substituents is preferably the para or ortho position.

Examples of the aromatic heterocyclic group include pyridyl, pyrrolyl, furyl and thienyl groups.

At least one of $R^1$ to $R^3$ is a group represented by the formula (2).

Specific examples of the groups represented by $R^4$ and $R^5$ are as follows.

Examples of the C3-C8 alkyl groups include branched-chain and cyclic alkyl groups with 3 to 8 carbon atoms, such as isopropyl, sec-butyl, tert-butyl, tert-pentyl, cyclopentyl and cyclohexyl groups.

Preferable alkyl groups are branched-chain alkyl groups with 3 to 6 carbon atoms.

More preferable alkyl groups are isopropyl, sec-butyl and tert-butyl groups.

Examples of the aryl groups are the same as those given above.

Examples of the substituted aryl groups include aryl groups substituted with a C1-C8 alkyl group, a halogen atom, a hydroxyl group, an alkoxy group, an amino group, a nitro group, a cyano group, a carbonyl-containing group represented by —COR$^a$ (R$^a$=a C1-C8 alkyl group, an aryl group, a C1-C8 alkoxy group or an aryloxy group), a sulfonyl group or a trifluoromethyl group.

Preferable substituted aryl groups are 2,6-xylyl and 2,4,6-mesityl groups.

Specific examples of the groups represented by $R^6$ to $R^8$ are as follows.

Examples of the C1-C8 alkyl groups are the same as those given above.

Examples of the aryl groups are the same as those given above.

Examples of the substituted aryl group are the same as those given above.

Preferable examples of the organobismuth compound represented by the formula (1) are compounds in which $R^1$ represents a compound represented by the formula (2), $R^2$ and $R^3$ each represent a C1-C4 alkyl group or a phenyl group, $R^4$ and $R^5$ each represent a C3-C6 alkyl group or an aryl group, and $R^6$ to $R^8$ each represent a hydrogen atom.

Especially preferable examples of the organobismuth compounds represented by the formula (1) are compounds in which $R^1$ represents a compound represented by the formula (2), $R^2$ and $R^3$ each represent a C1-C4 alkyl group, $R^4$ and $R^5$ each represent a C3-C6 alkyl group or an aryl group, and $R^6$ to $R^8$ each represent a hydrogen atom.

Specific examples of the organobismuth compounds represented by the formula (1) are as follows: (2,6-diisopropylphenylthio)dimethylbismuthane, (2,4,6-triisopropylphenylthio)dimethylbismuthane, (2,6-di-sec-butylphenylthio)dimethylbismuthane, (2,6-di-tert-butylphenylthio)dimethylbismuthane, (2,4,6-tri-tert-butylphenylthio)dimethylbismuthane, (2,6-dicyclohexylphenylthio)dimethylbismuthane, (2,6-diphenylphenylthio)dimethylbismuthane, (2,6-di-o-tolylphenylthio)dimethylbismuthane, (2,6-di-m-tolylphenylthio)dimethylbismuthane, (2,6-di-p-tolylphenylthio)dimethylbismuthane, [2,6-bis(o-methoxyphenyl)phenylthio]dimethylbismuthane, [2,6-bis(m-methoxyphenyl)phenylthio]dimethylbismuthane, [2,6-bis(p-methoxyphenyl)phenylthio]dimethylbismuthane, (2,6-di-2,6-xylylphenylthio)dimethylbismuthane, (2,6-di-2,4-xylylphenylthio)dimethylbismuthane, (2,6-di-2,3-xylylphenylthio)dimethylbismuthane, (2,6-di-2,4,6-mesitylphenylthio)dimethylbismuthane, [2,6-bis(2,6-diisopropylphenyl)phenylthio]dimethylbismuthane, [2,6-bis(bis(trimethylsilyl)methyl)phenylthio]dimethylbismuthane, [2,4,6-tris(bis(trimethylsilyl)methyl)phenylthio]dimethylbismuthane, [2,6-bis(tris(trimethylsilyl)methyl)phenylthio]dimethylbismuthane, and [2,4,6-tris(tris(trimethylsilyl)methyl)phenylthio]dimethylbismuthane.

Specific examples of the organobismuth compounds also include all of compounds in which dimethylbismuthane in the above compounds is replaced with diethylbismuthane, di-n-propylbismuthane or diphenylbismuthane, and still also include: bis(2,6-diisopropylphenylthio)methylbismuthane, bis(2,4,6-triisopropylphenylthio)methylbismuthane, bis(2,6-di-sec-butylphenylthio)methylbismuthane, bis(2,6-di-tert-butylphenylthio)methylbismuthane, bis(2,4,6-tri-tert-butylphenylthio)methylbismuthane, bis(2,6-dicyclohexylphenylthio)methylbismuthane, bis(2,6-diphenylphenylthio)methylbismuthane, bis(2,6-di-o-tolylphenylthio)methylbismuthane, bis(2,6-di-m-tolylphenylthio)methylbismuthane, bis(2,6-di-p-tolylphenylthio)methylbismuthane, bis[2,6-bis(o-methoxyphenyl)phenylthio]methylbismuthane, bis[2,6-bis(m-methoxyphenyl)phenylthio]methylbismuthane, bis[2,6-bis(p-methoxyphenyl)phenylthio]methylbismuthane, bis(2,6-di-2,6-xylylphenylthio)methylbismuthane, bis(2,6-di-2,5-xylylphenylthio)methylbismuthane, bis(2,6-di-2,4-xylylphenylthio)methylbismuthane, bis(2,6-di-2,3-xylylphenylthio)methylbismuthane, bis(2,6-di-2,4,6-mesitylphenylthio)methylbismuthane, bis[2,6-bis(2,6-diisopropylphenyl)phenylthio]methylbismuthane, bis[2,6-bis(bis(trimethylsilyl)methyl)phenylthio]methylbismuthane, bis[2,4,6-tris(bis(trimethylsilyl)methyl)phenylthio]methylbismuthane, bis[2,6-bis(tris(trimethylsilyl)methyl)phenylthio]methylbismuthane, and bis[2,4,6-tris(tris(trimethylsilyl)methyl)phenylthio]methylbismuthane.

Specific examples of the organobismuth compounds also include all of the compound in which methylbismuthane in the above compounds is replaced with ethylbismuthane, n-propylbismuthane or phenylbismuthane, and still also include: tris(2,6-diisopropylphenylthio)bismuthane, tris(2,4,6-triisopropylphenylthio)bismuthane, tris(2,6-di-sec-butylphenylthio)bismuthane, tris(2,6-di-tert-butylphenylthio)bismuthane, tris(2,4,6-tri-tert-butylphenylthio)bismuthane, tris(2,6-dicyclohexylphenylthio)bismuthane, tris(2,6-diphenylphenylthio)bismuthane, tris(2,6-di-o-tolylphenylthio)bismuthane, tris(2,6-di-m-tolylphenylthio)bismuthane, tris(2,6-di-p-tolylphenylthio)bismuthane, tris[2,6-bis(o-methoxyphenyl)phenylthio]bismuthane, tris[2,6-bis(m- methoxyphenyl)phenylthio]bismuthane, tris[2,6-bis(p-methoxyphenyl)phenylthio]bismuthane, tris(2,6-di-2,6-xylylphenylthio)bismuthane, tris(2,6-di-2,5-xylylphenylthio)bismuthane, tris(2,6-di-2,4-xylylphenylthio)bismuthane, tris(2,6-di-2,3-xylylphenylthio)bismuthane, tris(2,6-di-2,4,6-mesitylphenylthio)bismuthane, tris[2,6-bis(2,6-diisopropylphenyl)phenylthio]bismuthane, tris[2,6-bis(bis(trimethylsilyl)methyl)phenylthio]bismuthane, tris[2,4,6-tris(bis(trimethylsilyl)methyl)phenylthio]bismuthane, tris[2,6-bis(tris(trimethylsilyl)methyl)phenylthio]bismuthane, and tris[2,4,6-tris(tris(trimethylsilyl)methyl)phenylthio]bismuthane.

The organobismuth compound represented by the formula (1) can be prepared by reacting a compound represented by the formula (3) with a compound represented by the formula (4)

  (3)

wherein X represents a halogen atom, a C1-C8 alkyl group, an aryl group, a substituted aryl group or an aromatic heterocyclic group where at least one of Xs is a halogen atom,

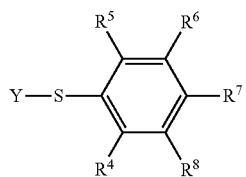  (4)

wherein Y represents a hydrogen atom or an alkali metal, $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

Specific examples of the groups represented by X are as follows.

Examples of the C1-C8 alkyl groups, aryl groups, substituted aryl groups and aromatic heterocyclic groups are the same as those for $R^1$.

Examples of the halogen atoms include fluorine, chlorine, bromine and iodine atoms.

The compound of the formula (3) is synthesized, for example, by disproportionation between trialkylbismuthane and bismuth trihalide as described in Chem. Rev. vol. 82, pp. 15 (1982).

Specific examples of the compounds (3) include dimethylbismuthanyl bromide, diethylbismuthanyl bromide, di-n-butylbismuthanyl bromide, diphenylbismuthanyl bromide, methyldibromobismuthane, ethyldibromobismuthane, n-butyldibromobismuthane, phenyldibromobismuthane, and bismuth tribromide.

Specific examples of the compounds (3) also include all of the compound in which bromide in the above compounds is replaced with chloride or iodide.

A specific example of the methods for preparing a compound represented by the formula (3) and containing one or two halogen atoms is as follows.

Bismuth trihalide is dissolved or suspended in a solvent. Examples of usable solvents include ethers, such as dialkyl ether, tetrahydrofuran (THF) and dimethoxyethane, aromatic solvents, such as toluene and xylene, and aliphatic hydrocarbons, such as hexane. Preferable solvents are diethyl ether and THF. The amount of solvent used is suitably adjusted, but is generally 1 to 100 ml and preferably 5 to 20 ml per g of bismuth trihalide.

Trialkylbismuthane is dissolved in a solvent. Examples of usable solvents include ethers, such as dialkyl ether, tetrahydrofuran (THF) and dimethoxyethane, and aromatic solvents, such as toluene and xylene. Preferable solvents are diethyl ether and THF. The amount of solvent used is suitably adjusted, but is generally 1 to 100 ml and preferably 5 to 20 ml per g of trialkylbismuthane. This solution is slowly added to the above solution of bismuth trihalide, and then stirred.

The reaction time varies depending on the reaction temperature and pressure, but is generally 5 minutes to 24 hours and preferably 10 minutes to 2 hours. The reaction temperature is −150° C. to 40° C., preferably −100° C. to 40° C., more preferably −78° C. to 40° C., and still more preferably 0° C. to 20° C. The pressure is generally atmospheric pressure, but may be increased or reduced.

The ratio between trialkylbismuthane and bismuth trihalide is 0.4 to 2.5 mol, preferably 0.5 to 2.0 mol, of bismuth trihalide with respect to 1 mol of trialkylbismuthane.

After the completion of the reaction, it can be suitably selected whether the compound of the formula (3) is used directly from the reaction solution or it is isolated and purified depending on the compound. The purification method can be suitably selected depending on the compound, but is generally preferably attained by distillation or recrystallization.

Specific examples of trialkylbismuthane include trimethylbismuthane, triethylbismuthane, tri-n-propylbismuthane, tri-n-butylbismuthane, and triphenylbismuthane.

A specific example of methods for preparing trialkylbismuthane is as follows.

Bismuth trihalide is dissolved or suspended in a solvent. Examples of usable solvents include ethers, such as dialkyl ether, tetrahydrofuran (THF) and dimethoxyethane, aromatic solvents, such as toluene and xylene, and aliphatic hydrocarbons, such as hexane. Preferable solvents are diethyl ether and THF. The amount of solvent used is suitably adjusted, but is generally 1 to 100 ml and preferably 5 to 20 ml per g of bismuth trihalide. To this solution is slowly added dropwise a solution of alkylating agent, followed by stirring.

Examples of alkylating agent include alkyllithium and a solution of Grignard reagent.

Solvents for alkylating agent include ethers, such as dialkyl ether, tetrahydrofuran (THF) and dimethoxyethane, and aliphatic hydrocarbons, such as hexane. Preferable solvents are diethyl ether and THF. The concentration of alkylating agent is preferably 1.0 to 3.0 M.

The reaction time varies depending on the reaction temperature and pressure, but is generally 5 minutes to 24 hours and preferably 10 minutes to 2 hours. The reaction temperature is −150° C. to 40° C., preferably −100° C. to 40° C., more preferably −78° C. to 40° C., and still more preferably 0° C. to 20° C. The pressure is generally atmospheric pressure, but may be increased or reduced.

The ratio between bismuth trihalide and alkylating agent is 2.5 to 6.0 mol, preferably 3.0 to 4.5 mol, of alkylating agent with respect to 1 mol of bismuth trihalide.

After the completion of the reaction, the solvent is concentrated to isolate and purify trialkylbismuthane. The purification method can be suitably selected depending on the compound, but is generally preferably attained by distillation.

Specific examples of the groups represented by Y are as follows.

Examples of the alkali metals include lithium, sodium and potassium. The compound of the formula (4) is synthesized, for example, by the reaction of iodobenzene derivative with sulfur as described in Angew. Chem. Int. Ed. vol. 33, pp. 1178 (1994).

Specific examples of the compounds (4) include: 2,6-diisopropylbenzenethiol, 2,4,6-triisopropylbenzenethiol, 2,6-di-sec-butylbenzenethiol, 2,6-di-tert-butylbenzenethiol, 2,4,6-tri-tert-butylbenzenethiol, 2,6-dicyclohexylbenzenethiol, 2,6-diphenylbenzenethiol, 2,6-di-o-tolylbenzenethiol, 2,6-di-m-tolylbenzenethiol, 2,6-di-p-tolylbenzenethiol, 2,6-bis(o-methoxyphenyl)benzenethiol, 2,6-bis(m-methoxyphenyl)benzenethiol, 2,6-bis(p-methoxyphenyl)benzenethiol, 2,6-di-2,6-xylylbenzenethiol, 2,6-di-2,5-xylylbenzenethiol, 2,6-di-2,4-xylylphenylbenzenethiol, 2,6-di-2,3-xylylphenylbenzenethiol, 2,6-di-2,4,6-mesitylbenzenethiol, 2,6-bis(2,6-diisopropylphenyl)benzenethiol, 2,6-bis(2,6-diisopropylphenyl)benzenethiol, 2,6-bis(bis(trimethylsilyl)methyl)benzenethiol, 2,4,6-tris(bis(trimethylsilyl)methyl)benzenethiol, 2,6-bis(tris(trimethylsilyl)methyl)benzenethiol, and 2,4,6-tris(tris(trimethylsilyl)methyl)benzenethiol. Specific examples of the compound also include all of the compounds in which bromide in the above compounds is replaced with chloride or iodide.

Specific examples of the compounds (4) also include all of compounds in which a hydrogen atom in a —SH group of thiol in the above compounds is substituted with sodium, lithium or potassium.

The organobismuth compound which is represented by the formula (1) and in which one of $R^1$ to $R^3$ is a group represented by the formula (2) can be prepared by reacting compounds represented by the formula (5) and the formula (6)

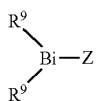

(5)

wherein Z represents an alkali metal or $BiR^9{}_2$ where $R^9$ represents a C1-C8 alkyl group, an aryl group or a substituted aryl group

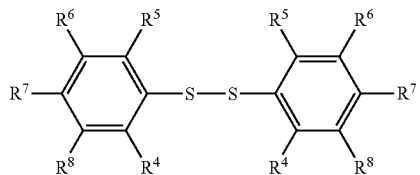

(6)

wherein $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group.

Specific examples of the group represented by Z are as follows.

Examples of the alkali metal include sodium, potassium and lithium.

Examples of the $BiR^9{}_2$ group include dimethylbismuthanyl, diethylbismuthanyl, di-n-butylbismuthanyl, and diphenylbismuthanyl groups.

Examples of the C1-C8 alkyl groups are the same as those for $R^1$.

Examples of the aryl groups are the same as those for $R^1$.

Examples of the substituted aryl groups are the same as those for $R^1$.

The compound of the formula (5) is synthesized, for example, by the reaction of trialkylbismuthane with an alkali metal as described in Organometallics. vol. 1, pp. 1408 (1982).

Specific examples of the compounds (5) include dimethylbismuthanylsodium, diethylbismuthanylsodium, di-n-butylbismuthanylsodium, diphenylbismuthanylsodium, tetramethyldibismuthane, tetraethyldibismuthane, tetra-n-butyldibismuthane, and tetraphenyldibismuthane. Specific examples of the compounds (5) also include all of the compounds in which sodium in the above compounds is replaced with lithium or potassium.

Specific examples of the groups represented by $R^4$ to $R^8$ are the same as those for the formula (4).

The compound of the formula (6) is synthesized by oxidizing the thiol compound of the formula (4).

Specific examples of the compounds (6) include: bis(2,6-diisopropylphenyl)disulfide, bis(2,4,6-triisopropylphenyl)disulfide, bis(2,6-di-sec-butylphenyl)disulfide, bis(2,6-di-tert-butylphenyl)disulfide, bis(2,4,6-tri-tert-butylphenyl)disulfide, bis(2,6-dicyclohexylphenyl)disulfide, bis(2,6-diphenylphenyl)disulfide, bis(2,6-di-o-tolylphenyl)disulfide, bis(2,6-di-m-tolylphenyl)disulfide, bis(2,6-di-p-tolylphenyl)disulfide, bis[2,6-bis(o-methoxyphenyl)phenyl]disulfide, bis[2,6-bis(m-methoxyphenyl)phenyl]disulfide, bis[2,6-bis(p-methoxyphenyl)phenyl]disulfide, bis(2,6-di-2,6-xylylphenyl)disulfide, bis(2,6-di-2,5-xylylphenyl)disulfide, bis(2,6-di-2,4-xylylphenyl)disulfide, bis(2,6-di-2,3-xylylphenyl)disulfide, bis(2,6-di-2,4,6-mesitylphenyl)disulfide, bis[2,6-bis(2,6-diisopropylphenyl)phenyl]disulfide, bis[2,6-bis(bis(trimethylsilyl)methyl)phenyl]disulfide, bis[2,4,6-tris(bis(trimethylsilyl)methyl)phenyl]disulfide, bis[2,6-bis(tris(trimethylsilyl)methyl)phenyl] disulfide, and bis[2,4,6-tris(tris(trimethylsilyl)methyl)phenyl]disulfide.

A specific example of methods for preparing the compound represented by the formula (1) is as follows.

(A) Method Using Compound Represented by the Formula (3) and Compound Represented by the Formula (4)

A compound represented by the formula (4) is dissolved or suspended in a solvent. Examples of usable solvents include amines, such as N,N-diethylamine and pyridine, ethers, such as dialkyl ether, tetrahydrofuran (THF) and dimethoxyethane, aromatic solvents, such as toluene and xylene, and aliphatic hydrocarbons, such as hexane. Preferable solvents are diethyl ether and THF. The amount of solvent used is suitably adjusted, but is generally 1 to 100 ml and preferably 5 to 20 ml per g of the compound (4).

To this solution is slowly added the compound represented by the formula (3), followed by stirring. The compound of the formula (3) may be dissolved in a solvent and then added to the above solution. Examples of usable solvents include ethers, such as dialkyl ether, tetrahydrofuran (THF) and dimethoxyethane. A preferable solvent is THF. The amount of solvent used is suitably adjusted, but is generally 0 to 100 ml and preferably 0 to 20 ml per g of the compound (4). The reaction time varies depending on the reaction temperature and pressure, but is generally 5 minutes to 24 hours and preferably 10 minutes to 2 hours. The reaction temperature is −150° C. to 40° C., preferably −100° C. to 40° C., more preferably −78° C. to 40° C., and still more preferably 0° C. to 20° C. The pressure is generally atmospheric pressure, but may be increased or reduced.

The ratio between the compound (3) and the compound (4) is 0.5 to 4.5 mol of compound (4) with respect to 1 mol of compound (3), and preferably 1.0 to 3.0 mol of compound (6) with respect to 1 mol of compound (3).

After the completion of the reaction, the solvent is concentrated to isolate and purify the desired compound. The purification method can be suitably selected depending on the compound, but is generally preferably attained by recrystallization.

(B) Method Using Compound Represented by the Formula (5) and Compound Represented by the Formula (6)

The compound represented by the formula (5) is dissolved or suspended in a solvent. Examples of such solvents usable include liquid ammonia, a mixed solvent of liquid ammonia and tetrahydrofuran, a mixed solvent of liquid ammonia and ether, a mixed solvent of liquid ammonia and 1,4-dioxane, ethers such as tetrahydrofuran, ether and 1,4-dioxane, and aliphatic hydrocarbons such as pentane and hexane. The amount of solvent used is suitably adjusted, but is generally 30 to 100 ml and preferably 10 to 30 ml per g of the compound (5). The compound represented by the formula (6) is dissolved in a solvent. Examples of such solvents usable include ethers, such as dialkyl ether, tetrahydrofuran (THF) and dimethoxyethane, and aromatic solvents, such as toluene and xylene. The amount of solvent used is suitably adjusted, but is generally 1 to 100 ml and preferably 5 to 20 ml per g of the compound (6). This solution is slowly added dropwise to the solution of the compound (5), and then stirred. The reaction time varies depending on the reaction temperature and pressure, but is generally 5 minutes to 24 hours and preferably 10 minutes to 2 hours. The reaction temperature is −78° C. to 40° C., preferably −78° C. to 30° C., and more preferably −40° C. to 20° C. The pressure is generally atmospheric pressure, but may be increased or reduced.

The ratio between the compound (5) and the compound (6) is 0.5 to 1.5 mol, preferably 0.8 to 1.2 mol, of compound (6) with respect to 1 mol of compound (5). After the completion of the reaction, the solvent is concentrated to isolate and purify the desired compound. The purification method can be suitably selected depending on the compound, but is generally preferably attained by recrystallization.

In the present invention, for example, an organobismuth compound represented by the formula (7) or an organotellurium compound represented by the formula (8) can be used as a living radical polymerization initiator.

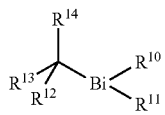

(7)

wherein $R^{10}$ and $R^{11}$ each represent a C1-C8 alkyl group, an aryl group, a substituted aryl group or an aromatic heterocyclic group, $R^{12}$ and $R^{13}$ each represent a hydrogen atom or a C1-C8 alkyl group, and $R^{14}$ represents an aryl group, a substituted aryl group, an aromatic heterocyclic group, an acyl group, an amido group, an oxycarbonyl group or a cyano group.

Specific examples of the groups represented by $R^{10}$ and $R^{11}$ are as follows.

Examples of the C1-C8 alkyl group include straight-chain, branched-chain and cyclic alkyl groups of 1 to 8 carbon atoms, such as methyl, ethyl, n-propyl, isopropyl, cyclopropyl, n-butyl, sec-butyl, tert-butyl, cyclobutyl, n-pentyl, n-hexyl, n-heptyl and n-octyl groups.

Preferable alkyl groups are straight- and branched-chain alkyl groups with 1 to 4 carbon atoms.

More preferable are methyl, ethyl and n-butyl group.

Examples of the aryl group include phenyl and naphtyl groups.

A preferable aryl group is a phenyl group.

Examples of the substituted aryl group include substituent-containing phenyl and substituent-containing naphtyl groups.

Examples of the substituents in such a substituent-containing aryl group include a halogen atom, hydroxy, alkoxy, amino, nitro and cyano groups, a carbonyl-containing group represented by —$COR^a$ ($R^a$=a C1-C8 alkyl group, an aryl group, a C1-C8 alkoxy group or an aryloxy group), a sulfonyl group, and a trifluoromethyl group.

A preferable substituted aryl group is a trifluoromethyl-substituted phenyl group.

The number of substituents is preferably one or two, and the position of substituents is preferably the para or ortho position.

Examples of the aromatic heterocyclic group include pyridyl, pyrrole, furyl and thienyl groups.

Specific examples of the groups represented by $R^{12}$ and $R^{13}$ are as follows.

Examples of the C1-C8 alkyl groups are the same as those listed for $R^{10}$.

Specific examples of the group represented by $R^{14}$ are as follows.

Examples of the aryl group, substituted aryl group and aromatic heterocyclic group are the same as those listed for $R^{10}$.

Examples of the acyl group include formyl, acetyl and benzoyl groups.

Examples of the amido group include carboxamido such as acetamido, malonamido, succinamido, maleamido, benzamido and 2-furamido, thioamido such as thioacetamido, hexanedithioamido, thiobenzamido and methanethiosulfonamido, selenoamido such as selenoacetamido, hexanediselenoamido, selenobenzamido and methaneselenosulfonamido, and N-substituted amido such as N-methylacetamido, benzanilido, cyclohexanecarboxanilido and 2,4'-dichloroacetanilido.

Examples of the oxycarbonyl group include groups represented by —$COOR^b$ (where $R^b$=H, a C1-C8 alkyl group or an aryl group).

Specific examples of the oxycarbonyl groups include carboxyl, methoxycarbonyl, ethoxycarbonyl, propoxycarbonyl, n-butoxycarbonyl, sec-butoxycarbonyl, tert-butoxycarbonyl, n-pentoxycarbonyl and phenoxycarbonyl groups.

Preferable oxycarbonyl groups are methoxycarbonyl and ethoxycarbonyl groups.

Preferable groups represented by $R^{14}$ are aryl, substituted aryl, oxycarbonyl and cyano groups.

A preferable aryl group is a phenyl group.

Preferable substituted aryl groups are a halogen-substituted phenyl group and a trifluoromethyl-substituted phenyl group.

When the substituent is a halogen atom, the number of substituents is preferably one to five. When the substituent is an alkoxy or trifluoromethyl group, the number of substituents is preferably one or two. If the number of substituents is one, the position of the substituent is preferably the para or ortho position. If the number of substituents is two, the position of the substituents is preferably the meta position.

Preferable oxycarbonyl groups are methoxycarbonyl and ethoxycarbonyl groups.

Preferable organobismuth compounds represented by the formula (7) are the compounds in which $R^{10}$ and $R^{11}$ each represent a C1-C4 alkyl group, $R^{12}$ and $R^{13}$ each represent a hydrogen atom or a C1-C4 alkyl group, and $R^{14}$ represents an aryl group, a substituted aryl group or an oxycarbonyl group.

Especially preferable organobismuth compounds are the compounds in which $R^{10}$ and $R^{11}$ each represent a C1-C4 alkyl group, $R^{12}$ and $R^{13}$ each represent a hydrogen atom or a C1-C4 alkyl group, and $R^{14}$ represents a phenyl, substituted-phenyl, methoxycarbonyl or ethoxycarbonyl group.

Specific examples of the organobismuth compounds represented by the formula (7) are as follows: (Dimethylbismuthanyl-methyl)benzene, (dimethylbismuthanyl-methyl)

naphthalene, 1-chloro-4-(dimethylbismuthanyl-methyl)benzene, 1-hydroxy-4-(dimethylbismuthanyl-methyl)benzene, 1-methoxy-4-(dimethylbismuthanyl-methyl)benzene, 1-amino-4-(dimethylbismuthanyl-methyl)benzene, 1-nitro-4-(dimethylbismuthanyl-methyl)benzene, 1-cyano-4-(dimethylbismuthanyl-methyl)benzene, 1-methylcarbonyl-4-(dimethylbismuthanyl-methyl)benzene, 1-phenylcarbonyl-4-(dimethylbismuthanyl-methyl)benzene, 1-methoxycarbonyl-4-(dimethylbismuthanyl-methyl)benzene, 1-phenoxycarbonyl-4-(dimethylbismuthanyl-methyl)benzene, 1-sulfonyl-4-(dimethylbismuthanyl-methyl)benzene, 1-trifluoromethyl-4-(dimethylbismuthanyl-methyl)benzene, 3,5-bis-trifluoromethyl-1-(dimethylbismuthanyl-methyl)benzene, 1,2,3,4,5-pentafluoro-6-(dimethylbismuthanyl-methyl)benzene, 2-(dimethylbismuthanyl-methyl)pyridine, 1-(dimethylbismuthanyl-methyl)-1H-pyrrole, 2-(dimethylbismuthanyl-methyl)furan, 2-(dimethylbismuthanyl-methyl)thiophene, (dimethylbismuthanyl)acetaldehyde, 1-(dimethylbismuthanyl)propane-2-one, 2-(dimethylbismuthanyl)-1-phenyl-ethanone, (dimethylbismuthanyl)acetate, methyl dimethylbismuthanyl-acetate, ethyl dimethylbismuthanyl-acetate, n-propyl dimethylbismuthanyl-acetate, n-butyl dimethylbismuthanyl-acetate, phenyl dimethylbismuthanyl-acetate, (dimethylbismuthanyl)acetonitrile, (1-dimethylbismuthanyl-ethyl)benzene, (1-dimethylbismuthanyl-ethyl)naphthalene, 1-chloro-4-(1-dimethylbismuthanyl-ethyl)benzene, 1-hydroxy-4-(1-dimethylbismuthanyl-ethyl)benzene, 1-methoxy-4-(1-dimethylbismuthanyl-ethyl)benzene, 1-amino-4-(1-dimethylbismuthanyl-ethyl)benzene, 1-nitro-4-(1-dimethylbismuthanyl-ethyl)benzene, 1-cyano-4-(1-dimethylbismuthanyl-ethyl)benzene, 1-methylcarbonyl-4-(1-dimethylbismuthanyl-ethyl)benzene, 1-phenylcarbonyl-4-(1-dimethylbismuthanyl-ethyl)benzene, 1-methoxycarbonyl-4-(1-dimethylbismuthanyl-ethyl)benzene, 1-phenoxycarbonyl-4-(1-dimethylbismuthanyl-ethyl)benzene, 1-sulfonyl-4-(1-dimethylbismuthanyl-ethyl)benzene, 1-trifluoromethyl-4-(1-dimethylbismuthanyl-ethyl)benzene, 3,5-bis-trifluoromethyl-1-(1-dimethylbismuthanyl-ethyl)benzene, 1,2,3,4,5-pentafluoro-6-(1-dimethylbismuthanyl-ethyl)benzene, 2-(1-dimethylbismuthanyl-ethyl)pyridine, 1-(1-dimethylbismuthanyl-ethyl)-1H-pyrrole, 2-(1-dimethylbismuthanyl-ethyl)furan, 2-(1-dimethylbismuthanyl-ethyl)thiophene, 2-dimethylbismuthanyl-propionaldehyde, 3-dimethylbismuthanyl-butane-2-one, 2-dimethylbismuthanyl-1-phenyl-propane-1-one, 2-dimethylbismuthanyl-propionate, methyl 2-dimethylbismuthanyl-propionate, ethyl 2-dimethylbismuthanyl-propionate, n-propyl 2-dimethylbismuthanyl-propionate, n-butyl 2-dimethylbismuthanyl-propionate, phenyl 2-dimethylbismuthanyl-propionate, 2-dimethylbismuthanyl-propionitrile, (2-dimethylbismuthanyl-propyl)benzene, (2-dimethylbismuthanyl-propyl)naphthalene, 1-chloro-4-(1-dimethylbismuthanyl-1-methyl-ethyl)benzene, 1-hydroxy-4-(1-dimethylbismuthanyl-1-methyl-ethyl)benzene, 1-methoxy-4-(1-dimethylbismuthanyl-1-methyl-ethyl)benzene, 1-amino-4-(1-dimethylbismuthanyl-1-methyl-ethyl)benzene, 1-nitro-4-(1-dimethylbismuthanyl-1-methyl-ethyl)benzene, 1-cyano-4-(1-dimethylbismuthanyl-1-methyl-ethyl)benzene, 1-methylcarbonyl-4-(1-dimethylbismuthanyl-1-methyl-ethyl)benzene, 1-phenylcarbonyl-4-(1-dimethylbismuthanyl-1-methyl-ethyl)benzene, 1-methoxycarbonyl-4-(1-dimethylbismuthanyl-1-methyl-ethyl)benzene, 1-phenoxycarbonyl-4-(1-dimethylbismuthanyl-1-methyl-ethyl)benzene, 1-sulfonyl-4-(1-dimethylbismuthanyl-1-methyl-ethyl)benzene, 1-trifluoromethyl-4-(1-dimethylbismuthanyl-1-methyl-ethyl)benzene, 3,5-bis-trifluoromethyl-1-(1-dimethylbismuthanyl-1-methyl-ethyl)benzene, 1,2,3,4,5-pentafluoro-6-(1-dimethylbismuthanyl-1-methyl-ethyl)benzene, 2-(1-dimethylbismuthanyl-1-methyl-ethyl)pyridine, 1-(1-dimethylbismuthanyl-1-methyl-ethyl)-1H-pyrrole, 2-(1-dimethylbismuthanyl-1-methyl-ethyl)furan, 2-(1-dimethylbismuthanyl-1-methyl-ethyl)thiophene, 2-dimethylbismuthanyl-2-methyl-propionaldehyde, 3-dimethylbismuthanyl-3-methyl-butane-2-one, 2-dimethylbismuthanyl-2-methyl-1-phenyl-propane-1-one, 2-dimethylbismuthanyl-2-methyl-propionate, methyl 2-dimethylbismuthanyl-2-methyl-propionate, ethyl 2-dimethylbismuthanyl-2-methyl-propionate, n-propyl 2-dimethylbismuthanyl-2-methyl-propionate, n-butyl 2-dimethylbismuthanyl-2-methyl-propionate, phenyl 2-dimethylbismuthanyl-2-methyl-propionate, and 2-dimethylbismuthanyl-2-methyl-propionitrile.

Examples of the organobismuth compounds also include all of compounds in which dimethylbismuthanyl in the above compounds is replaced with diethylbismuthanyl, di-n-propylbismuthanyl or diphenylbismuthanyl.

For example, an organotellurium compound represented by the formula (8) can be used as a living radical polymerization initiator used in the present invention

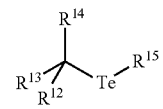

(8)

wherein $R^{15}$ represents a C1-C8 alkyl group, an aryl group, a substituted aryl group or an aromatic heterocyclic group, $R^{12}$ and $R^{13}$ each represent a hydrogen atom or a C1-C8 alkyl group, and $R^{14}$ represents an aryl group, a substituted aryl group, an aromatic heterocyclic group, an acyl group, an amido group, an oxycarbonyl group or a cyano group.

Examples of the groups represented by $R^{12}$ to $R^{14}$ are the same as those given above.

Examples of the group represented by $R^{15}$ are the same as those for $R^{10}$.

Specific representative examples of the organotellurium compounds represented by the formula (8) are as follows: (Methyltelluromethyl)benzene, (1-methyltelluroethyl)benzene, 1-chloro-4-(1-methyltelluroethyl)benzene, 1-trifluoromethyl-4-(1-methyltelluroethyl)benzene, 3,5-bis-trifluoromethyl-1-(1-methyltelluroethyl)benzene, 1,2,3,4,5-pentafluoro-6-(1-methyltelluroethyl)benzene, 2-methyltelluropropionitrile, (2-methyltelluropropyl)benzene, methyl 2-methyltelluro-2-methyl-propionate, ethyl 2-methyltelluro-2-methyl-propionate, and 2-methyltelluro-2-methyl-propionitrile. Examples of the organotellurium compounds also include all of the compounds in which methyltelluro is replaced with ethyltelluro, n-butyltelluro, n-octyltelluro or the like. In addition to these, all of the organotellurium compounds described in WO 2004/014962 can be taken as examples of the above compound.

In the present invention, an azo polymerization initiator can be used in order to promote the polymerization rate. The azo polymerization initiator can be used without particular limitation insofar as it is usable in usual radical polymerization.

Example thereof include 2,2'-azobis-isobutyronitrile (AIBN), 2,2'-azobis(2-methylbutyronitrile) (AMBN), 2,2'-azobis(2,4-dimethylvaleronitrile) (ADVN), 1,1'-azobis(1-cyclohexanecarbonitrile) (ACHN), dimethyl-2,2'-azobisisobutyrate (MAIB), 4,4'-azobis(4-cyanovaleric acid)

(ACVA), 1,1'-azobis(1-acetoxy-1-phenylethane), 2,2'-azobis (2-methylbutylamide), 2,2'-azobis(4-methoxy-2,4-dimethylvaleronitrile), 2,2'-azobis(2-methylamidinopropane) dihydrochloride, 2,2'-azobis[2-(2-imidazoline-2-yl)propane], 2,2'-azobis[2-methyl-N-(2-hydroxyethyl)propionamide], 2,2'-azobis(2,4,4-trimethylpentane), 2-cyano-2-propylazoformamide, 2,2'-azobis(N-butyl-2-methylpropionamide), and 2,2'-azobis(N-cyclohexyl-2-methylpropionamide).

These azo polymerization initiators are preferably suitably selected depending on the reaction conditions. For example, for low temperature polymerization (at not more than 40° C.), 2,2'-azobis(2,4-dimethylvaleronitrile) (ADVN) or 2,2'-azobis(4-methoxy-2,4-dimethylvaleronitrile) is preferably used. For middle temperature polymerization (at 40 to 80° C.), 2,2'-azobis-isobutyronitrile (AIBN), 2,2'-azobis(2-methylbutyronitrile) (AMBN), dimethyl-2,2'-azobisisobutyrate (MAIB), 1,1'-azobis(1-acetoxy-1-phenylethane), 4,4'-azobis (4-cyanovaleric acid) (ACVA), 2,2'-azobis(2-methylbutylamide), 2,2'-azobis(2-methylamidinopropane)dihydrochloride or 2,2'-azobis[2-(2-imidazoline-2-yl)propane] is preferably used. For high temperature polymerization (at not less than 80° C.), 1,1'-azobis(1-cyclohexanecarbonitrile) (ACHN), 2-cyano-2-propylazoformamide, 2,2'-azobis(N-butyl-2-methylpropionamide), 2,2'-azobis(N-cyclohexyl-2-methylpropionamide), 2,2'-azobis(2,4,4-trimethylpentane) or 2,2'-azobis[2-methyl-N-(2-hydroxyethyl)propionamide] is preferably used.

The vinyl monomer usable in the present invention is not particularly limited insofar as it can be subjected to radical polymerization.

Examples of the vinyl monomers are as follows:

(Meth)acrylic acid esters, such as methyl (meth)acrylate, ethyl (meth)acrylate, propyl (meth)acrylate, butyl (meth) acrylate, octyl (meth)acrylate, lauryl (meth)acrylate and (meth)acrylic acid 2-hydroxyethyl; cycloalkyl-containing unsaturated monomers, such as cyclohexyl (meth)acrylate, methylcyclohexyl (meth)acrylate, isobornyl (meth)acrylate and cyclododecyl (meth)acrylate;

Carboxyl-containing unsaturated monomers, such as (meth)acrylic acid methyl, maleic acid methyl, fumaric acid methyl, itaconic acid methyl, citraconic acid methyl, crotonic acid methyl and maleic anhydride methyl;

Tertiary amine-containing unsaturated monomers, such as N,N-dimethylaminopropyl(meth)acrylamide, N,N-dimethylaminoethyl(meth)acrylamide, 2-(dimethylamino)ethyl (meth)acrylate, and N,N-dimethylaminopropyl (meth)acrylate;

Quaternary ammonium base-containing unsaturated monomers, such as N-2-hydroxy-3-acryloyloxypropyl-N,N, N-trimethylammonium chloride, and N-methacryloylaminoethyl-N,N,N-dimethylbenzylammonium chloride;

Epoxy-containing unsaturated monomers, such as glycidyl (meth)acrylate;

Aromatic unsaturated monomers (styrene monomers), such as styrene, α-methylstyrene, 4-methylstyrene (p-methylstyrene), 2-methylstyrene (o-methylstyrene), 3-methylstyrene (m-methylstyrene), 4-methoxystyrene (p-methoxystyrene), p-tert-butylstyrene, p-n-butylstyrene, p-tert-butoxystyrene, 2-hydroxymethylstyrene, 2-chlorostyrene (o-chlorostyrene), 4-chlorostyrene (p-chlorostyrene), 2,4-dichlorostyrene, 1-vinylnaphthalene, divinylbenzene, p-styrene sulfonic acid and alkali metal salts thereof (such as sodium salt and potassium salt);

Heterocyclic ring-containing unsaturated monomers, such as 2-vinylthiophene, N-methyl-2-vinylpyrrole, 1-vinyl-2-pyrrolidone, 2-vinylpyridine, and 4-vinylpyridine;

Vinylamides, such as N-vinylformamide and N-vinylacetamide;

(Meth)acrylamide monomers, such as (meth)acrylamide, N-methyl(meth)acrylamide, N-isopropyl(meth)acrylamide, and N,N-dimethyl(meth)acrylamide;

α-olefins, such as 1-hexene, 1-octene, and 1-decene;

Dienes, such as butadiene, isoprene, 4-methyl-1,4-hexadiene, and 7-methyl-1,6-octadiene; carboxylic acid esters, such as vinyl acetate and vinyl benzoate; hydroxyethyl (meth) acrylate; (meth)acrylonitrile; methyl vinyl ketone; vinyl chloride; and vinylidene chloride.

Preferable among them are (meth)acrylic acid esters, cycloalkyl-containing unsaturated monomers, aromatic unsaturated monomers (styrene monomers), (meth)acrylamide monomers, (meth)acrylonitrile and methyl vinyl ketone.

Examples of preferable (meth)acrylic acid ester monomers are methyl (meth)acrylate, ethyl (meth)acrylate, propyl (meth)acrylate, butyl (meth)acrylate and (meth)acrylic acid 2-hydroxyethyl. Especially preferable are methyl methacrylate, ethyl methacrylate, propyl methacrylate, butyl methacrylate and methacrylic acid 2-hydroxyethyl.

Preferable cycloalkyl-containing unsaturated monomers are cyclohexyl (meth)acrylate and isobornyl (meth)acrylate. Especially preferable are cyclohexyl methacrylate and isobornyl methacrylate.

Examples of preferable styrene monomers are styrene, α-methylstyrene, o-methylstyrene, p-methylstyrene, p-methoxystyrene, p-t-butylstyrene, p-n-butylstyrene, p-tert-butylstyrene, p-chlorostyrene, p-styrene sulfonic acid and alkali metal salts thereof (such as sodium salt and potassium salt). Especially preferable are styrene and p-chlorostyrene.

An example of preferable (meth)acrylamide monomers is N-isopropyl(meth)acrylamide. N-isopropylmethacrylamide is especially preferable.

The term "(meth)acrylic acid" as used above refers collectively to "acrylic acid" and "methacrylic acid".

The method for preparing a living radical polymer according to the present invention is specifically as follows.

A vinyl monomer, a living radical polymerization initiator represented by the formula (7), a radical polymerization promoter represented by the formula (1), and as required an azo polymerization initiator are mixed together in a container whose internal air is replaced with an inert gas. Next, the mixture is stirred. The reaction temperature and the reaction time may be suitably adjusted. The mixture is generally stirred at 20 to 150° C. for 1 minute to 100 hours, and preferably at 40 to 100° C. for 0.1 to 30 hours. In this case, the pressure is generally atmospheric pressure, but may be increased or reduced. Examples of the inert gases in this case include nitrogen, argon and helium. Preferable inert gases are argon and nitrogen. Nitrogen is especially preferred.

The ratio between the vinyl monomer and the living radical polymerization initiator represented by the formula (7) is suitably adjusted depending on the molecular weight and molecular weight distribution of a living radical polymer to be obtained, but the vinyl monomer is generally used in an amount of 5 to 10000 mol, preferably 50 to 5000 mol, with respect to 1 mol of the living radical polymerization initiator represented by the formula (7).

The ratio between the radical polymerization promoter represented by the formula (1) and the living radical polymerization initiator represented by the formula (7) is 0.05 to 0.5 mol, preferably 0.1 to 0.3 mol, of the radical polymerization promoter, with respect to 1 mol of the living radical polymerization initiator represented by the formula (7).

In using the living radical polymerization initiator represented by the formula (7), the living radical polymerization promoter represented by the formula (1) and the azo polymerization initiator in combination, the azo polymerization initiator is generally used in an amount of 0.01 to 100 mol, preferably 0.1 to 10 mol, especially preferably 0.1 to 5 mol, with respect to 1 mol of the living radical polymerization initiator, and the living radical polymerization promoter is generally used in an amount of 0.05 to 0.5 mol, preferably 0.1 to 0.3 mol, with respect to 1 mol of the living radical polymerization initiator. The vinyl monomer is used in an amount of 5 to 10000 mol, and preferably 50 to 5000 mol.

The reaction is generally conducted in the absence of solvent, but an organic solvent commonly used for radical polymerization or an aqueous solvent may be used. Examples of usable organic solvents include benzene, toluene, N,N-dimethylformamide (DMF), dimethyl sulfoxide (DMSO), acetone, 2-butanone (methyl ethyl ketone), dioxane, hexafluoroisopropanol, chloroform, carbon tetrachloride, tetrahydrofuran (THF), ethyl acetate, and trifluoromethylbenzene. Examples of aqueous solvents include water, methanol, ethanol, isopropanol, n-butanol, ethyl cellosolve, butyl cellosolve, 1-methoxy-2-propanol, and diacetone alcohol. The amount of the solvent used is suitably adjusted. For example, the solvent is used in an amount of 0.01 to 50 ml, preferably 0.05 to 10 ml, more preferably 0.1 to 1 ml, per gram of the vinyl monomer.

Next, the mixture is stirred. The reaction temperature and the reaction time are suitably adjusted depending on the molecular weight and molecular weight distribution of a living radical polymer to be obtained. The mixture is generally stirred at 0 to 150° C. for 1 minute to 100 hours, preferably at 20 to 100° C. for 0.1 to 30 hours, and more preferably at 20 to 80° C. for 0.1 to 15 hours. In this case, the pressure is generally atmospheric pressure, but may be increased or reduced.

After the completion of the reaction, the solvent used and the remaining monomer are removed under reduced pressure in the usual manner to extract the desired polymer, or the desired polymer is isolated by re-precipitation using a solvent in which the desired polymer is insoluble. The reaction can be conducted by any method insofar as it has no adverse effect on the desired polymer.

The organobismuth compound usable as an initiator in the present invention is stable towards water. Therefore, the polymer of the present invention can be synthesized by the following aqueous polymerization methods as described in Patent Document 2.

Specifically, an emulsion polymerization method uses a surfactant, wherein polymerization is conducted mainly in micelles. When required, a highly water-soluble polymer as a dispersant such as polyvinyl alcohol, may be used. One kind of such a surfactant can be used, or two or more kinds of such surfactants can be used in combination. The amount of such a surfactant used is preferably 0.3 to 50 parts by weight, more preferably 0.5 to 50 parts by weight, per 100 parts by weight of all monomers. The amount of water used is preferably 50 to 2000 parts by weight, more preferably 70 to 1500 parts by weight, per 100 parts by weight of all monomers. The polymerization temperature is not particularly limited, but is preferably in the range of 0 to 100° C. and more preferably 40 to 90° C. The reaction time is suitably determined to complete the polymerization reaction, such as depending on the reaction temperature, the monomer composition used or the kinds of surfactant and polymerization initiator, but is preferably within 24 hours.

A suspension polymerization method uses a dispersant, wherein polymerization is conducted mainly without using micelles. When required, together with the dispersant may be used a dispersion aid, such as sodium chloride, potassium chloride, sodium sulfate, potassium sulfate or manganese sulfate. The amount of such aqueous dispersion stabilizers used is preferably 0.01 to 30 parts by weight, more preferably 0.05 to 10 parts by weight, and especially preferably 0.1 to 5 parts by weight, per 100 parts by weight of all monomers. The amount of water used is preferably 50 to 2000 parts by weight, more preferably 70 to 1500 parts by weight, per 100 parts by weight of all monomers. The polymerization temperature is not particularly limited, but is preferably in the range of 0 to 100° C. and more preferably 40 to 90° C. The reaction time is suitably determined to complete the polymerization reaction, such as depending on the reaction temperature, the monomer composition used or the kinds of aqueous dispersion stabilizers and polymerization initiator, but is preferably within 24 hours.

A miniemulsion polymerization method uses a surfactant and a cosurfactant, wherein a monomer is forcibly dispersed using a homogenizer or ultrasonic device and then polymerized mainly without using micelles. The amount of such surfactant and cosurfactant used is 0.3 to 50 parts by weight, especially preferably 0.5 to 50 parts by weight, with respect to all monomers. The ultrasonic irradiation time is 0.1 to 10 minutes and especially preferably 0.2 to 5 minutes.

[Patent Document 2] Japanese Patent Application No. 2005-041321

The living radical polymer obtained according to the present invention is one synthesized by living radical polymerization. Therefore, if two or more kinds of vinyl monomers are reacted one after another, a block copolymer can be obtained. The block copolymer can be prepared, regardless of the kinds of monomers, depending on the order of monomers to be reacted. In obtaining a block copolymer by reacting a vinyl monomer A with a vinyl monomer B, an A-B diblock copolymer or a B-A diblock copolymer can be obtained depending on the order of reaction, and in turn, for example, an A-B-A triblock copolymer or an A-B-C-B-A pentablock copolymer can be obtained.

In the above preparation, the production of each monomer block may be followed directly by the reaction for the next monomer block, or the monomer block after the completion of reaction may be purified, followed by the start of the reaction for the next monomer block. The isolation of the block copolymer can be conducted in usual manners.

The molecular weight of living radical polymer obtained by the present invention can be adjusted according to the reaction time, the amount of compound of the formula (1) and the amount of compound of the formula (2). Thus, a living radical polymer having a number average molecular weight of 1000 to 2000000 can be obtained. In particular, the present invention is suitable for obtaining a high-molecular weight living radical polymer having a number average molecular weight of 100000 to 1000000.

The molecular weight distribution (PDI=Mw/Mn) of the living radical polymer obtained by the present invention is controlled within the range of 1.05 to 1.50. Furthermore, a living radical polymer having a narrower molecular weight distribution range of 1.05 to 1.30 or a still narrower molecular weight distribution range of 1.05 to 1.10 can be obtained.

BEST MODE FOR CARRYING OUT THE INVENTION

The present invention will be described below in detail with reference to Examples, but is not at all limited to them. In Examples and Comparative Examples, various properties were determined with the following instruments.

$^1$H-NMR: Varian Mercury plus (400 MHz)

Molecular Weight and Molecular Weight Distribution:
Instrument: Gel Permeation Chromatography Shodex GPC-104
Column: Shodex KF-602 and Shodex KF-603

SYNTHESIS EXAMPLE 1

Synthesis of 1,3-Dibromoiodobenzene

A 65 mL solution of n-butyllithium (1.6M hexane solution, 105 mmol), a hexane solution thereof (made by Tokyo Chemical Industry Co., Ltd.), was added to 100 mL of THF, and the mixture was cooled to −70° C. To the mixture was slowly added dropwise at −70° C. 14.7 mL (105 mmol) of diisopropylamine (Aldrich), followed by stirring for 30 minutes at −70° C. To the reaction mixture was slowly added dropwise at −70° C. 12.7 mL (105 mmol) of 1,3-dibromobenzene (Tokyo Chemical Industry Co., Ltd.), followed by stirring for 2 hours at −70° C. In 50 mL of THF was dissolved 26.7 g (105 mmol) of iodine (Wako Pure Chemical Industries, Ltd.). This liquid was added dropwise to the above reaction liquid of 1,3-dibromobenzene at −70° C., and the mixture was slowly warmed to room temperature. The solvent was removed under reduced pressure from the mixture, and the residue was dissolved in diethyl ether. To the solution was added a saturated aqueous solution of sodium thiosulfate, followed by separation and drying of the organic layer with magnesium sulfate.

MgSO$_4$ and the solvent were removed, and the residue was recrystallized from methanol, giving 34.6 g of white crystals of 1,3-dibromobenzene (91% in yield).

It was confirmed that the product was 1,3-dibromobenzene by $^1$H-NMR.

$^1$H-NMR (400 MHz, CDCl$_3$) 7.07 (t, J=8.0 Hz, 1H, p-H), 7.56 (d, J=8.0 Hz, 2H, m-H).

SYNTHESIS EXAMPLE 2

Synthesis of 2,6-Dimesityliodobenzene

A solvent of 200 mL of THF was added to 6.0 g (250 mmol) of magnesium (Wako Pure Chemical Industries, Ltd.) and a trace amount of iodine. In 100 mL of THF was dissolved 34 mL (225 mmol) of bromomesitylene (Wako Pure Chemical Industries, Ltd.). The solution was added dropwise to the above magnesium/THF slurry at room temperature in 2 hours. After the completion of the dropping, the solution was refluxed for 2 hours, and then cooled to room temperature. In 50 mL of THF was dissolved 23 g (64 mmol) of 1,3-dibromoiodobenzene. The solution was added dropwise to the above Grignard solution at room temperature in 1 hour. The reaction liquid was refluxed for 3 hours, and then cooled to 0° C. A solution of 25 g (100 mmol) of iodine in 50 mL of THF was added dropwise to the reaction mixture, followed by warming to room temperature. The reaction mixture was washed with a saturated aqueous solution of sodium sulfite, and then extracted three times with diethyl ether. The ether layers were mixed, then washed with water and saturated brine, and then dried with magnesium sulfate. The solvent was removed under reduced pressure, and the byproduct was then removed under reduced pressure. The residue was recrystallized from methanol, giving 19.7 g of white solid of 2,6-dimesityliodobenzene (70% in yield).

It was confirmed that the product was 2,6-dimesityliodobenzene by $^1$H-NMR.

$^1$H-NMR (400 MHz, CDCl$_3$) 1.98 (s, 12H, o-CH$_3$), 2.35 (s, 6H, p-CH$_3$), 6.96 [s, 4H, m-H (Mes)], 7.08 [d, J=7.6 Hz, 2H, m-H (Ph)], 7.46 [t, J=7.6 Hz, 1H, p-H (Ph)].

SYNTHESIS EXAMPLE 3

Synthesis of 2,6-dimesitylbenzenethiol

In 400 mL of THF was dissolved 22 g (50 mmol) of 2,6-dimesityliodobenzene. The solution was cooled to −78° C. To the liquid was slowly added dropwise 34 mL of n-butyllithium (a 1.6M hexane solution, 55 mmol), which is a hexane solution made by Tokyo Chemical Industry Co., Ltd. The mixture was stirred at −78° C. for 1 hour, followed by addition of 4.8 g (150 mmol) of sulfur (Wako Pure Chemical Industries, Ltd.) and stirring at −78° C. for 2 hours. An excessive amount of LiAlH$_4$ (Wako Pure Chemical Industries, Ltd.) was suspended in diethyl ether, and the above liquid containing 22 g (50 mmol) of 2,6-dimesityliodobenzene was added dropwise to the suspension. The mixture was stirred at room temperature for 12 hours. Then, the excessive amount of LiAlH$_4$ was quenched with 10% hydrochloric acid. The mixture was extracted three times with diethyl ether, and the extract was dried with potassium carbonate. The residue was recrystallized from ethyl acetate, giving 9.4 g of white solid of 2,6-dimesitylbenzenethiol (54% in yield).

It was confirmed that the product was 2,6-dimesitylbenzenethiol by $^1$H-NMR.

$^1$H-NMR (400 MHz, CDCl$_3$) 2.02 (s, 12H, o-CH$_3$), 2.34 (s, 6H, p-CH$_3$), 3.02 (s, 1H, S—H), 6.98 [s, 4H, m-H (Mes)], 7.03 [d, J=7.6 Hz, 2H, m-H (Ph)], 7.23 [t, J=7.6 Hz, 1H, p-H (Ph)].

SYNTHESIS EXAMPLE 4

Synthesis of Trimethylbismuthane

Under argon gas atmosphere, a solution of 25 g of bismuth tribromide in 40 ml of THF was added dropwise to a 1.0 M diethyl ether solution of methyllithium to keep reflux. Thereafter, the mixture was stirred at room temperature for 1.5 hours. The solvent was evaporated under atmospheric pressure, followed by the distillation of the desired compound. The obtained distillate was distilled again, giving 8.1 g of colorless oily material (54.8% in yield).

It was confirmed that the product was the desired one by $^1$H-NMR.

$^1$H-NMR (300 MHz, CDCl$_3$) 1.13 (s, 9H)

SYNTHESIS EXAMPLE 5

Synthesis of Diphenylbismuthanyl Bromide

Under argon gas atmosphere, 22.014 g (50 mmol) of triphenylbimuthine (Tokyo Chemical Industry Co., Ltd.) was dissolved in 400 ml of THF. The solution was cooled to 0° C. and to the solution was slowly added (for 30 minutes) 11.231 g (25 mmol) of tribromobismuthine (Aldrich). The mixture was stirred for 1 hour while being warmed to room temperature, thereby separating yellow precipitate. The yellow precipitate was filtered and dried under reduced pressure. The precipitate obtained was recrystallized from benzene, giving 27.422 g (62 mmol: yield 83%) of yellow powder.

It was confirmed that the product was the desired one by $^1$H-NMR.

¹H-NMR (400 MHz) 7.12 (tt, J=1.2 Hz, J=7.4 Hz, aromatic proton), 7.33 (tt, J=1.2 Hz, J=7.6 Hz, 4H, aromatic proton), 8.02 (ddd, J=0.8 Hz, J=1.6 Hz, J=6.4 Hz, 4H, aromatic proton).

SYNTHESIS EXAMPLE 6

Synthesis of Dimethylbismuthanyl Bromide

Under argon gas atmosphere, a solution of 7.2 g of bismuth tribromide in 13 ml of THF was added dropwise to 8.0 g (31.5 mmol) of trimethylbismuthane synthesized in Synthesis Example 4. Thereafter, the mixture was stirred at room temperature for 1.5 hours. The reaction solution was filtrated with 0.2 µm membrane filter and, then, THF was removed under reduced pressure, giving 14.23 g of light yellow amorphous (94.5% in yield).

It was confirmed that the product was the desired one by ¹H-NMR.

¹H-NMR (300 MHz, DMSO) 1.52 (s, 6H)

SYNTHESIS EXAMPLE 7

Synthesis of Methyl 2-Dimethylbismuthanyl-2-methyl-propionate

Under argon gas atmosphere, 2.86 g (28 mmol) of methyl isobutyrate was dissolved in 25 ml of THF, and the solution was cooled to −78° C. To the solution was slowly added dropwise (for 10 minutes) 14.0 ml (28 mmol) of lithium diisopropylamide (Aldrich, a 2.0M heptane/THF/ethylbenzene solution thereof). While the mixture was gradually warmed (for 1 hour), the solution of 8.9 g of dimethylbismuthanyl bromide synthesized in Synthesis Example 6 in 25 ml of THF was added dropwise within the range of −40° C. to −30° C. to the mixture. Thereafter, the reaction solution was stirred until the solution temperature reached 0° C. (for 1 hour). The solids precipitated in the reaction solution were filtered off with quartz wool, THF was removed under reduced pressure, and the product was distilled under reduced pressure, giving 4.45 g of yellow oily material (46.7% yield, bp 59° C./2.0 mmHg). It was confirmed that the product was the desired one by MS (GCMS), ¹H-NMR and ¹³C-NMR.

¹H-NMR (300 MHz, CDCl$_3$) 1.08 (s, 6H, BiMe$_2$), 1.78 (s, 6H, CMe$_2$), 3.72 (s, 3H, COOMe)

¹³C-NMR (300 MHz, CDCl$_3$) 10.12 (BiMe$_2$), 24.13 (Mex2), 33.11 (Bi—C, quaternary carbon), 50.72 (OMe), 178.34 (C=O) GCMS (EI+) m/z: Calcd for C$_7$H$_{15}$O$_2$Bi (M)+, 340; Found 340

EXAMPLE 1

In 30 mL of diethyl ether was dissolved 5.8 g (17 mmol) of 2,6-dimesitylbenzenethiol, and to the solution was slowly added dropwise at −78° C. 34 mL of n-butyllithium (a 1.6M hexane solution, 17 mmol), which is a hexane solution made by Tokyo Chemical Industry Co., Ltd. The mixture was stirred at −78° C. for 1 hour, and warmed to room temperature in 1 hour.

To the reaction mixture was added at 0° C. 6.7 g (15 mmol) of diphenylbismuthanyl bromide), followed by stirring at room temperature for 2 hours. The reaction mixture was washed with water, saturated aqueous ammonium chloride and brine, and then the organic layer was dried with magnesium sulfate. The precipitated solid was removed by Celite filtration, the solvent was removed under reduced pressure, and then the residue was recrystallized from chloroform/hexane. Thus, 7.3 g of light yellow crystals were obtained.

The obtained product was identified as 2,6-dimesitylphenylthio) diphenylbismuthane by ¹H-NMR, ¹³C-NMR, HRMS and IR.

¹H-NMR (400 MHz, CDCl$_3$) 2.02 (s, 12H, o-CH$_3$), 2.31 (s, 6H, p-CH$_3$), 6.86 [s, 4H, m-H (Mes)], 7.12 [d, J=7.6 Hz, 2H, m-H (S-Ph)], 7.19 [t, J=7.6 Hz, 2H, p-H (Bi-Ph)], 7.28 [t, J=7.6 Hz, 1H, p-H (S-Ph)], 7.29 [d, J=7.6 Hz, 4H, m-H (Bi-Ph)], 7.45 [d, J=6.8 Hz, 4H, m-H (Bi-Ph]; ¹³C-NMR (100 MHz, CDCl$_3$) 21.00, 21.12, 127.19, 127.56, 128.01, 128.29, 128.84, 130.67, 133.85, 135.82, 136.48, 136.94, 139.38, 146.64; HRMS (EI) m/z: Calcd for C$_7$H$_{15}$O$_2$Bi (M)+, 708.2262; Found 708.2255; IR(neat) 815, 1135, 1185, 1270, 1460, 1695, 2940.

EXAMPLES 2 to 8

Synthesis of Polystyrene

Styrene (Sigma-Aldrich Japan K.K.), methyl 2-dimethylbismuthanyl-2-methyl-propionate (Bi initiator) (0.1 mmol) synthesized in Synthesis Example 7, (2,6-dimesitylphenylthio)diphenylbismuthane (0.02 mmol) synthesized in Example 1 and 2,2'-azobis-isobutyronitrile (0.02 mmol) were stirred, at the ratios and under the reaction conditions (time and temperature) as shown in Table 1, in a glove box with the internal air replaced with nitrogen.

After the completion of the reaction, the reaction mixture was dissolved in 4 ml of chloroform and then the solution was poured into 200 ml of methanol being stirred. The resulting polymer precipitate was filtered by suction and dried to give polystyrene.

Results of GPC analysis (with reference to the molecular weight of an authentic sample of polystyrene) are given in Table 1.

TABLE 1

| Example | Monomer (mmol) | Reaction Temp. (° C.) | Reaction Time (hr.) | Yield (%) | Mn | PDI |
|---|---|---|---|---|---|---|
| 2 | 10 | 60 | 24 | 96 | 10900 | 1.07 |
| 3 | 20 | 60 | 32 | 99 | 24700 | 1.09 |
| 4 | 50 | 60 | 60 | 99 | 55500 | 1.10 |
| 5 | 70 | 60 | 72 | 100 | 79500 | 1.10 |
| 6 | 100 | 60 | 84 | 98 | 103400 | 1.11 |
| 7 | 200 | 60 | 96 | 94 | 198100 | 1.14 |
| 8 | 1000 | 60 | 120 | 85 | 718100 | 1.29 |

EXAMPLES 9 to 12

Synthesis of Poly(n-Butyl Acrylate)

Stirred were n-Butyl acrylate (Sigma-Aldrich Japan K.K.), methyl 2-dimethylbismuthanyl-2-methyl-propionate (Bi initiator) (0.1 mmol) synthesized in Synthesis Example 7, (2,6-dimesitylphenylthio)diphenylbismuthane (0.02 mmol) synthesized in Example 1 and 2,2'-azobis-isobutyronitrile (0.02 mmol), at the ratios and under the reaction conditions (time and temperature) as shown in Table 2, in a glove box with the internal air replaced with nitrogen.

After the completion of the reaction, the reaction mixture was dissolved in 4 ml of chloroform and then the solution was poured into 200 ml of methanol being stirred. The resulting polymer precipitate was filtered by suction and dried to give poly(n-butyl acrylate).

Results of GPC analysis (with reference to the molecular weight of an authentic sample of poly(methyl methacrylate)) are given in Table 2.

TABLE 2

| Example | Monomer (mmol) | Reaction Temp. (° C.) | Reaction Time (hr.) | Yield (%) | Mn | PDI |
|---|---|---|---|---|---|---|
| 9 | 10 | 60 | 0.5 | 82 | 11600 | 1.06 |
| 10 | 25 | 60 | 1 | 82 | 31000 | 1.08 |
| 11 | 100 | 60 | 2 | 82 | 131000 | 1.12 |
| 12 | 1000 | 60 | 6 | 58 | 735400 | 1.20 |

EXAMPLES 13 to 16

Synthesis of Poly(Methyl Methacrylate)

Methyl methacrylate (Sigma-Aldrich Japan K.K.), methyl 2-dimethylbismuthanyl-2-methyl-propionate (Bi initiator) (0.1 mmol) synthesized in Synthesis Example 7 and (2,6-dimesitylphenylthio)diphenylbismuthane (0.02 mmol) synthesized in Example 1 were stirred, at the ratios and under the reaction conditions (time and temperature) as shown in Table 3, in a glove box with the internal air replaced with nitrogen.

After the completion of the reaction, the reaction mixture was dissolved in 10 ml of tetrahydrofuran and then the solution was poured into 200 ml of methanol being stirred. The resulting polymer precipitate was filtered by suction and dried to give poly(methyl methacrylate).

Results of GPC analysis (with reference to the molecular weight of an authentic sample of poly(methyl methacrylate)) are given in Table 3.

TABLE 3

| Example | Monomer (mmol) | Reaction Temp. (° C.) | Reaction Time (hr.) | Yield (%) | Mn | PDI |
|---|---|---|---|---|---|---|
| 13 | 10 | 60 | 5 | 99 | 10600 | 1.10 |
| 14 | 20 | 60 | 6 | 100 | 23100 | 1.09 |
| 15 | 50 | 60 | 8 | 98 | 53300 | 1.13 |
| 16 | 100 | 60 | 12 | 100 | 102900 | 1.16 |

EXAMPLE 17

Methyl methacrylate (the same as above) (20 mmol) and methyl 2-dimethylbismuthanyl-2-methyl-propionate (Bi initiator) (0.1 mmol) synthesized in Synthesis Example 7 were stirred at 100° C. for 3 hours in a glove box with the internal air replaced with nitrogen.

After the completion of the reaction, poly(methyl methacrylate) was obtained in 99% yield. GPC analysis revealed Mn=19900 and PDI=1.11.

Next, the obtained poly(methyl methacrylate) (0.1 mmol) (macroinitiator), styrene (the same as above) (100 mmol), (2,6-dimesitylphenylthio)diphenylbismuthane (0.02 mmol) synthesized in Example 1 and 2,2'-azobis-isobutyronitrile were stirred at 60° C. for 48 hours.

After the completion of the reaction, methyl methacrylate-styrene diblock copolymer was obtained in 98% yield. GPC analysis revealed Mn=126000 and PDI=1.19.

EXAMPLE 18

Styrene (the same as above) (12.5 mmol), methyl 2-dimethylbismuthanyl-2-methyl-propionate (Bi initiator) (0.05 mmol) synthesized in Synthesis Example 7, (2,6-dimesitylphenylthio)diphenylbismuthane (0.01 mmol) synthesized in Example 1 and 2,2'-azobis-isobutyronitrile (0.01 mmol) were stirred at 60° C. for 32 hours in a glove box with the internal air replaced with nitrogen. After the completion of the reaction, polystyrene was obtained in 98% yield. GPC analysis (with reference to the molecular weight of an authentic sample of polystyrene) revealed Mn=28700 and PDI=1.10.

Next, the obtained polystyrene (0.025 mmol) (macroinitiator), n-butyl acrylate (the same as above) (6.25 mmol), 2,2'-azobis-isobutyronitrile (0.005 mmol) and α,α,α-trifluoromethylbenzene (2 ml) were stirred at 60° C. for 20 hours. After the completion of the reaction, styrene-n-butyl acrylate diblock copolymer was obtained in 49% yield. GPC analysis (with reference to the molecular weight of an authentic sample of polystyrene) revealed Mn=45000 and PDI=1.20.

EXAMPLE 19

Synthesis of Poly(n-Butyl Acrylate)

N-Butyl acrylate (the same as above) (87 mmol), ethyl 2-methyltelluro-2-methyl-propionate (Te initiator: Otsuka Chemical Co., Ltd.) (0.046 mmol), (2,6-dimesitylphenylthio)diphenylbismuthane (0.0085 mmol) synthesized in Example 1 and 2,2'-azobis-isobutyronitrile (0.0085 mmol) were stirred at 60° C. for 4 hours in a glove box with the internal air replaced with nitrogen.

After the completion of the reaction, the reaction mixture was dissolved in 4 ml of chloroform and then the solution was poured into 200 ml of methanol being stirred. The resulting polymer precipitate was filtered by suction and dried to give poly(n-butyl acrylate) in 58% yield.

GPC analysis (with reference to the molecular weight of an authentic sample of polystyrene) revealed Mn=102300 and PDI=1.28.

INDUSTRIAL APPLICABILITY

The living radical polymerization promoter of the present invention enables precise control of the molecular weight and molecular weight distribution (PDI=Mw/Mn) of even a high-molecular weight polymer having a number average molecular weight of 100000 or more by polymerizing a vinyl monomer using the living radical polymerization promoter.

The invention claimed is:

1. An organobismuth compound represented by the formula (1)

wherein $R^1$ to $R^3$ each represent a C1-C8 alkyl group, an aryl group, a substituted aryl group, an aromatic heterocyclic group or a group represented by the formula (2) where at least one of $R^1$ and $R^2$ is a group represented by the following formula (2)

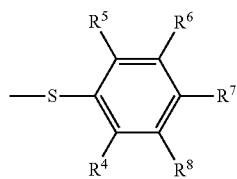

(2)

wherein $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group, and $R^3$ is a group other than the at least one of $R^1$ and $R^2$.

2. A method for preparing the organobismuth compound represented by the formula (1) according to claim 1, the method comprising reacting a compound represented by the formula (3) with a compound represented by the formula (4)

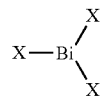

(3)

wherein X represents a halogen atom, a C1-C8 alkyl group, an aryl group, a substituted aryl group or an aromatic heterocyclic group where at least one of Xs is a halogen atom,

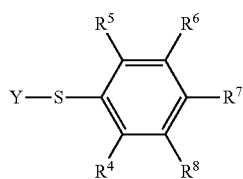

(4)

wherein Y represents a hydrogen atom or an alkali metal, $R^4$ and $R^5$ each represent a C3-C8 alkyl group, an aryl group or a substituted aryl group, and $R^6$ to $R^8$ each represent a hydrogen atom, a C1-C8 alkyl group, an aryl group or a substituted aryl group, to obtain the organobismuth compound according to claim 1.

3. A radical polymerization promoter being a compound represented by the formula (1) according to claim 1.

4. A method for preparing a living radical polymer, the method comprising polymerizing a vinyl monomer using a living radical polymerization initiator and a compound represented by the formula (1) according to claim 1.

5. The method for preparing a living radical polymer of claim 4, wherein the living radical polymerization initiator is an organobismuth compound represented by the formula (7)

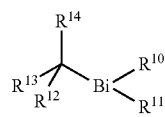

(7)

wherein $R^{10}$ and $R^{11}$ each represent a C1-C8 alkyl group, an aryl group, a substituted aryl group or an aromatic heterocyclic group, $R^{12}$ and $R^{13}$ each represent a hydrogen atom or a C1-C8 alkyl group, and $R^{14}$ represents an aryl group, a substituted aryl group, an aromatic heterocyclic group, an acyl group, an amido group, an oxycarbonyl group or a cyano group.

6. The method for preparing a living radical polymer of claim 4, wherein the living radical polymerization initiator is an organotellurium compound represented by the formula (8)

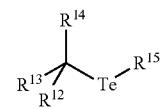

(8)

wherein $R^{15}$ represents a C1-C8 alkyl group, an aryl group, a substituted aryl group or an aromatic heterocyclic group, $R^{12}$ and $R^{13}$ each represent a hydrogen atom or a C1-C8 alkyl group, and $R^{14}$ represents an aryl group, a substituted aryl group, an aromatic heterocyclic group, an acyl group, an amido group, an oxycarbonyl group or a cyano group.

7. A living radical polymer obtained by polymerizing a vinyl monomer using a living radical polymerization initiator and a compound represented by the formula (1) according to claim 1.

8. A mixture of a living radical polymerization initiator and a compound represented by the formula (1) according to claim 1.

9. The organobismuth compound according to claim 1, wherein $R^1$ represents a group represented by the formula (2), and $R^2$ and $R^3$ each represent a C1-C4 alkyl group or a phenyl group.

* * * * *